US012508428B2

(12) United States Patent
Hoffman et al.

(10) Patent No.: US 12,508,428 B2
(45) Date of Patent: Dec. 30, 2025

(54) RESPIRATORY-BASED CARDIAC REMODELING PACING THERAPY

(71) Applicant: Medtronic, Inc., Minneapolis, MN (US)

(72) Inventors: Matthew J. Hoffman, St. Paul, MN (US); Troy E. Jackson, Rogers, MN (US); Michael D. Eggen, Chisago City, MN (US)

(73) Assignee: Medtronic, Inc., Minneapolis, MN (US)

( * ) Notice: Subject to any disclaimer, the term of this patent is extended or adjusted under 35 U.S.C. 154(b) by 372 days.

(21) Appl. No.: 18/101,799

(22) Filed: Jan. 26, 2023

(65) Prior Publication Data

US 2024/0252826 A1 Aug. 1, 2024

(51) Int. Cl.
*A61N 1/365* (2006.01)
*A61N 1/37* (2006.01)

(52) U.S. Cl.
CPC ....... *A61N 1/36514* (2013.01); *A61N 1/3702* (2013.01)

(58) Field of Classification Search
CPC . A61N 1/3702; A61N 1/36514; A61B 5/0816
See application file for complete search history.

(56) References Cited

U.S. PATENT DOCUMENTS

| | | | |
|---|---|---|---|
| 4,428,378 | A | 1/1984 | Anderson et al. |
| 4,567,892 | A | 2/1986 | Plicchi et al. |
| 4,644,954 | A | 2/1987 | Wittkampf et al. |
| 4,867,161 | A | 9/1989 | Schaldach |
| 4,884,576 | A | 12/1989 | Alt |
| 5,052,388 | A | 10/1991 | Sivula et al. |
| 5,052,454 | A | 10/1991 | Meinhardt |
| 5,097,831 | A | 3/1992 | Lekholm |
| 5,197,467 | A | 3/1993 | Steinhaus et al. |
| 5,292,340 | A | 3/1994 | Crosby et al. |
| 5,318,597 | A | 6/1994 | Hauck et al. |
| 5,876,353 | A | 3/1999 | Riff |
| 6,141,590 | A | 10/2000 | Renirie |
| 6,298,268 | B1 | 10/2001 | Ben-Haim et al. |
| 6,314,322 | B1 | 11/2001 | Rosenberg |

(Continued)

FOREIGN PATENT DOCUMENTS

| | | |
|---|---|---|
| EP | 2809393 | 12/2014 |
| EP | 4 054 708 B1 | 5/2023 |

(Continued)

OTHER PUBLICATIONS

International Search Report and Written Opinion for PCT/IB2024/050345 dated Mar. 26, 2024 (11 pages).

(Continued)

*Primary Examiner* — William J Levicky
(74) *Attorney, Agent, or Firm* — Mueting Raasch Group

(57) ABSTRACT

Systems, devices, and methods for performing respiratory-based cardiac remodeling pacing therapy are described in this disclosure. A patent's respiration may be monitored, and the lower pacing limit for the cardiac remodeling pacing and support pacing therapy delivered to a patient may be adjusted based on the monitored respiration to achieve or restore respiratory sinus arrhythmia.

30 Claims, 7 Drawing Sheets

(56) References Cited

U.S. PATENT DOCUMENTS 6,650,937 B2 11/2003 Kerver
7,133,718 B2 11/2006 Bakken et al.
7,194,306 B1 3/2007 Turcott
7,302,295 B2 11/2007 Stahmann
7,305,266 B1 12/2007 Kroll
7,445,605 B2 11/2008 Overall et al.
7,630,078 B1 12/2009 Nabutovsky et al.
7,660,616 B1 2/2010 Poore
7,769,451 B2 8/2010 Yang et al.
7,840,246 B1 11/2010 Poore
7,941,216 B2 5/2011 Salo et al.
8,027,724 B2 9/2011 Wei et al.
8,046,069 B2 10/2011 Kramer et al.
8,065,003 B2 11/2011 Kenknight et al.
8,126,549 B2 2/2012 Sigg et al.
8,306,615 B2 11/2012 Brockway et al.
8,386,038 B2 2/2013 Bianchi et al.
8,600,497 B1 12/2013 Yang et al.
8,798,751 B2 8/2014 Spear et al.
8,805,497 B2 8/2014 Dong et al.
8,996,101 B2 3/2015 Zhang et al.
9,002,454 B2 4/2015 Ghosh et al.
9,101,772 B2 8/2015 Kleckner et al.
9,155,896 B2 10/2015 Salo
9,320,906 B2 4/2016 Maskara et al.
9,403,016 B2 8/2016 Meyer
9,956,416 B2 5/2018 Ghosh et al.
10,029,103 B2 7/2018 Sweeney
10,702,698 B2 7/2020 Zhao et al.
11,207,529 B2 12/2021 Zhou
11,311,734 B2 4/2022 Zhou
2003/0158584 A1 8/2003 Cates et al.
2004/0199210 A1 10/2004 Shelchuk
2006/0100668 A1 5/2006 Ben-David
2006/0178586 A1 8/2006 Dobak
2006/0224196 A1 10/2006 Hettrick et al.
2006/0224203 A1 10/2006 Hettrick et al.
2006/0247692 A1 11/2006 Yang et al.
2007/0150017 A1 6/2007 Salo
2007/0203522 A1 8/2007 Hettrick et al.
2008/0051840 A1 2/2008 Moaddeb et al.
2008/0114408 A1 5/2008 Shuros et al.
2008/0119898 A1 5/2008 Ben-David et al.
2008/0132800 A1 6/2008 Hettrick et al.
2008/0188721 A1 8/2008 Patangay et al.
2008/0234776 A1 9/2008 Kenknight et al.
2009/0005831 A1 1/2009 Wilson et al.
2009/0093857 A1 4/2009 Markowitz et al.
2009/0234401 A1 9/2009 Zielinski et al.
2010/0016923 A1 1/2010 Rousso et al.
2010/0082077 A1 4/2010 Bruns
2010/0152802 A1 6/2010 Min
2010/0152804 A1 6/2010 Kleckner et al.
2012/0010674 A1 1/2012 Pastore et al.
2012/0035679 A1 2/2012 Dagan et al.
2012/0101541 A1 4/2012 Corbucci et al.
2012/0150252 A1 6/2012 Feldman et al.
2012/0290032 A1* 11/2012 Cho ....................... A61N 1/056 607/20
2012/0290033 A1* 11/2012 Cho ..................... A61N 1/3611 607/20
2012/0303078 A1 11/2012 Li et al.
2012/0323099 A1 12/2012 Mothilal et al.
2013/0237873 A1 9/2013 Zhang et al.
2014/0100621 A1 4/2014 Feldman et al.
2014/0277237 A1 9/2014 Maskara et al.
2014/0277240 A1 9/2014 Maskara et al.
2014/0303078 A1 10/2014 Melton et al.
2015/0250428 A1 9/2015 Zhang et al.
2016/0361559 A1 12/2016 Scharmer
2017/0079598 A1 3/2017 Stolen et al.
2017/0290550 A1 10/2017 Perschbacher et al.
2018/0126171 A1 5/2018 Herrmann et al.
2019/0167991 A1 6/2019 Stahmann et al.
2019/0168007 A1 6/2019 Stahmann et al.
2019/0201696 A1 7/2019 Koop et al.
2019/0336096 A1 11/2019 Itu et al.
2019/0381322 A1* 12/2019 Sharma .................. A61B 5/686
2019/0381323 A1 12/2019 Sharma et al.
2020/0038663 A1 2/2020 Meyer
2020/0289829 A1 9/2020 Ghosh

FOREIGN PATENT DOCUMENTS

WO 2005/039690 5/2005
WO 2005/118062 12/2005
WO 2008/109040 9/2008
WO 2013/010165 1/2013
WO 2018/067931 4/2018

OTHER PUBLICATIONS

Blain et al., "Influences of Breathing Patterns on Respiratory Sinus Arrhythmia in Humans During Exercise", Am J Physiol Heart Circ Physiol 288, H887-H895, 2005.
Boehmer et al., "A Multisensor Algorithm Predicts Heart Failure Events in Patients with Implanted Devices: Results from the MultiSense Study, JACC", Heart Failure, vol. 5, No. 3, 2017, pp. 216-225.
Gimelli et al., "CRT in Patients with Heart Failure: Time Course of Perfusion and Wall Motion Changes," 2010, Cardiology Research and Practice, 2010:981064, 5 pages.
Heidenreich, P.A., et al., Forecasting the impact of heart failure in the United States: a policy statement from the American Heart Association. Circ Heart Fail, 2013. 6(3): p. 606-19.
Hirsch et al., "Respiratory Sinus Arrhythmia in Humans: How Breathing Pattern Modulates Heart Rate," Department of Physiology, State University of New York at Buffalo, School of Medicine, Buffalo, New York, pp. H620-H629, 1981.
Infeld, Margaret, et al. "Personalized pacing (myPace): a new paradigm for diastolic heart failure treatment." Journal of the American College of Cardiology 77.18_Supplement_1 (2021): 223-223.
International Search Report and Written Opinion for PCT/US2021/037229 dated Oct. 29, 2019 (21 pages).
Jarvelainen et al., "Extracellular Matrix Molecules: Potential Targets in Pharmacotherapy," Pharmacol Rev, 2009, 61:198-223.
Jian, A., et al. "Association Between Heart Rate Variability and Echocardiographic Parameters in Heart Failure with Reduced and Preserved Ejection Fraction." Heart, Lung and Circulation 28 (2019): S161.
Klein, F.J., et al., Heart-Rate Induced Modifications of Concentric Left Ventricular Hypertrophy—Exploration of a Novel Therapeutic Concept. Am J Physiology, Published Sep. 2, 2016 vol. No. DOI: 10.1152/ajpheart.00301.2016.
Owan, T.E., et al., Trends in prevalence and outcome of heart failure with preserved ejection fraction. N Engl J Med, 2006. 355(3): p. 251-9.
Shanks, J., et al. "Reverse re-modelling chronic heart failure by reinstating heart rate variability." Basic Research in Cardiology 117.1 (2022): 1-16.
Solomon et al., "Effect of Cardiac Resynchronization Therapy on Reverse Remodeling and Relation to Outcome", American Heart Association, vol. 122, , Sep. 7, 2010, pp. 985-992.
Wahlberg K, Arnold ME, Lustgarten D, Meyer M. Effects of a Higher Heart Rate on Quality of Life and Functional Capacity in Patients With Left Ventricular Diastolic Dysfunction. Am J Cardiol. 2019;124(7):1069-75.
Westermann et al., "Role of left ventricular stiffness in heart failure with normal ejection fraction," Circulation, Apr. 22, 2008: 117 (16):2051-60.

* cited by examiner

RESPIRATORY-BASED CARDIAC REMODELING PACING THERAPY

The present disclosure is directed to respiratory-based cardiac remodeling pacing therapy, e.g., for treating heart failure (HF), and more specifically, systems, devices, and methods to perform such respiratory-based cardiac remodeling pacing therapy.

HF occurs when the heart muscle is unable to pump enough blood to meet the body's needs. The volume of blood pumped by the heart is determined by how well the heart squeezes (i.e., muscle contraction) and how well the heart relaxes and fills with blood. Ejection fraction is a measure of how much blood inside the left ventricle (LV) is pumped out with each contraction. When the left ventricle pumps, not all the blood in the ventricle leaves. A normal ejection fraction is more than about 50%. Heart failure with preserved ejection fraction (HFpEF) occurs when the left ventricle does not fill with blood as well as normal, but the ventricle can pump well. For example, the ventricle is stiff, or has thick walls, such that the ventricle does not relax to fill with a normal volume of blood. Alternatively, when the muscle contraction is abnormal (e.g., the muscle is too weak to pump properly), the condition is referred to as heart failure with reduced ejection fraction (HFrEF).

Patients with HFpEF represent nearly half of the heart failure population and continue to increase in prevalence relative to patients with HFrEF. Although patients with HFpEF experience outcomes as poor as those for patients with HFrEF, no evidence-based therapy to improve mortality and morbidity exists. The present technology is directed to algorithms for selecting a pacing therapy for a heart failure patient, such as one with HFpEF, based on monitored patient parameters that also account for interactions among various pacing therapies. The algorithms and pacing therapies may be implemented by implantable medical devices (IMDs) such as implantable cardioverter defibrillators (ICDs), cardiovascular implantable electronic devices (CIEDs), pacemakers, and cardiac resynchronization therapy (CRT) devices that, in some cases, include defibrillation capability (CRT-D devices).

SUMMARY

Embodiments described herein are directed to illustrative systems, devices, and methods to perform respiratory-based cardiac remodeling pacing therapy, e.g., for treating heart failure (HF), and more specifically, patients with HF with preserved ejection fraction (HFpEF). Generally, the illustrative systems, devices, and methods may be described as providing support pacing, cardiac remodeling pacing, and adjusting the pacing rate of each of the support pacing and cardiac remodeling pacing based on a patient's monitored, or measured, respiration to provide, or restore, respiratory sinus arrhythmia (RSA).

Moreover, the present disclosure may be further described as providing illustrative systems, devices, and methods that incorporate features that restore respiratory sinus arrhythmia while allowing for an elevated support rate with periods of cardiac remodeling pacing. By incorporating respiratory sinus arrhythmia along with cardiac remodeling pacing, not only does the illustrative systems, devices, and methods provide both features independently, but cardiac remodeling pacing may have enhanced efficacy by allowing for a higher proportion of the paced beats to fall within a therapeutic rate range (e.g., greater than 90 beats per minute), while potentially avoiding symptoms associated with sustained pacing at a higher rate. In at least one embodiment, the illustrative systems, devices, and methods may be described as providing a rate setting feature where the effective device lower rate is defined by a support rate, a maximum remodeling rate, and a respiratory sinus arrhythmia value or amplitude. The maximum remodeling rate may be defined as the maximum pacing rate when cardiac remodeling therapy criteria are met, and the support rate may be defined as the minimum effective device lower rate.

One illustrative implantable medical device may include a pacing electrode to be positioned proximate the patient's heart to deliver pacing therapy to the patient's heart, a respiration sensor to determine the patient's respiration rate, and a computing apparatus operably coupled to the pacing electrode and the respiration sensor. The computing apparatus may be configured to deliver pacing using at least the pacing electrode based on a lower rate limit, monitor the patient's respiration the respiration sensor, and adjust the lower rate limit based on the patient's respiration to restore respiratory sinus arrhythmia (RSA). Additionally, the computing apparatus may be further configured to increase the lower rate limit to provide cardiac remodeling pacing during remodeling time periods.

One illustrative method using, for example, an implantable medical device, may include delivering pacing to a patient's heart based on a lower rate limit, monitoring the patient's respiration, adjusting the lower rate limit based on the patient's respiration to restore respiratory sinus arrhythmia (RSA), and increasing the lower rate limit to provide cardiac remodeling pacing during remodeling time periods.

One illustrative implantable medical device may include a pacing electrode to be positioned proximate a patient's heart to deliver pacing therapy to the patient's heart, a respiration sensor to determine a respiration rate of the patient, and a computing apparatus operably coupled to the pacing electrode and the respiration sensor. The computing apparatus may be configured to switch between delivering support pacing using at least the pacing electrode based on a support pacing rate or delivering cardiac remodeling pacing using at least the pacing electrode to provide cardiac remodeling based on a cardiac remodeling pacing rate. The cardiac remodeling pacing rate may be greater than the support pacing rate. The computing apparatus may be further configured to monitor the patient's respiration rate using the respiration sensor and adjust the cardiac remodeling pacing rate and the support pacing rate based on the patient's respiration rate to restore respiratory sinus arrhythmia (RSA).

The above summary is not intended to describe each disclosed embodiment or every implementation of the present disclosure. The figures and the detailed description below more particularly exemplify illustrative embodiments.

BRIEF DESCRIPTION OF DRAWINGS

The discussion below refers to the following figures, wherein the same reference number may be used to identify the similar/same component in multiple figures. However, the use of a number to refer to a component in a given figure is not intended to limit the component in another figure labeled with the same number. The figures are not necessarily to scale.

DETAILED DESCRIPTION

Figure 1:
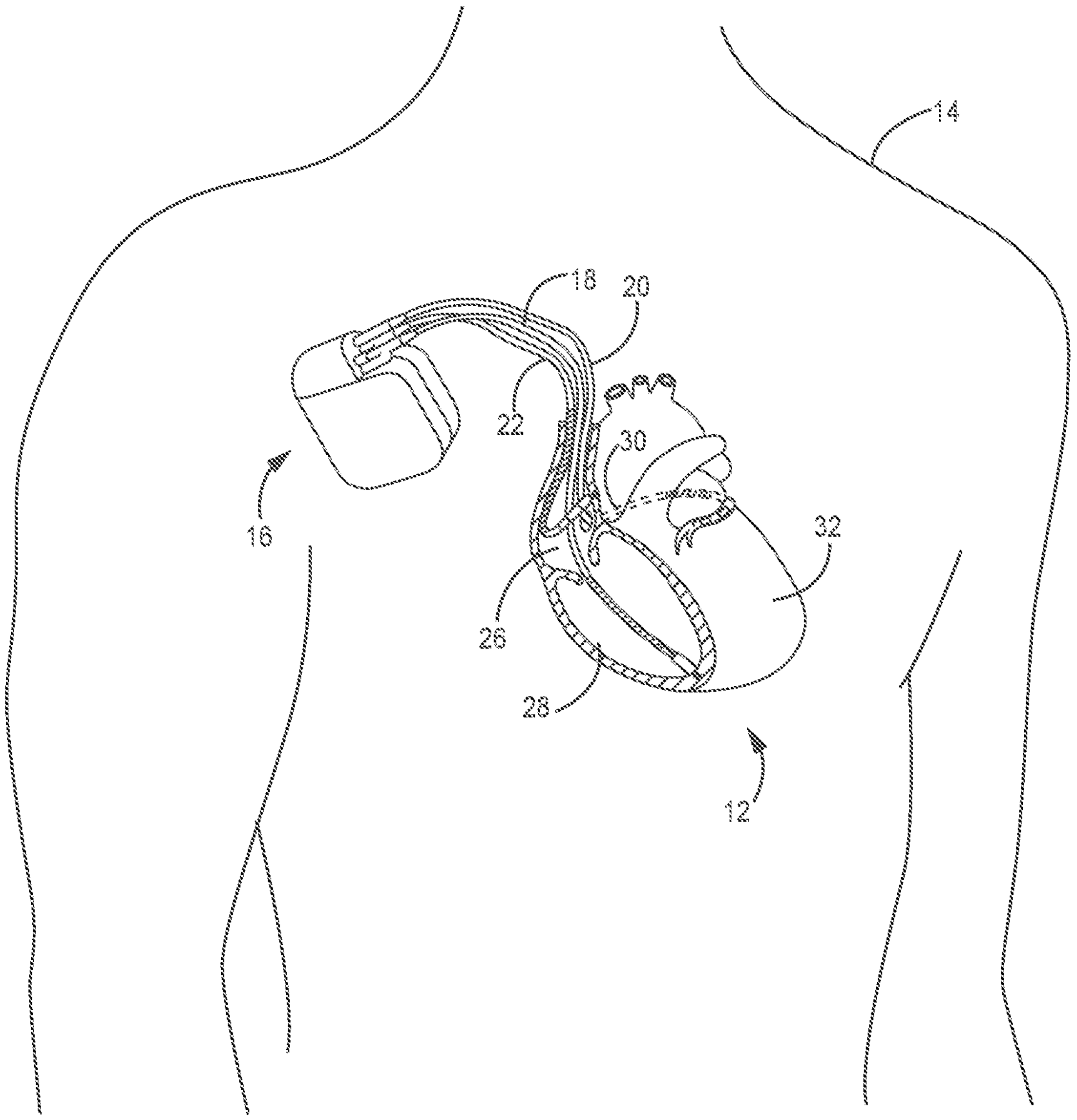
FIG. 1 is a diagram of a system including an IMD, in accordance with various embodiments described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized, and structural changes may be made without departing from (e.g., still falling within) the scope of the disclosure presented hereby.

Illustrative systems, devices, and methods shall be described with reference to FIGS. 1-6. It will be apparent to one skilled in the art that elements or processes from one embodiment may be used in combination with elements or processes of the other embodiments, and that the possible embodiments of such systems, devices, and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 is a conceptual diagram of an illustrative therapy system 10 that may be used to deliver pacing therapy, such as support pacing and cardiac remodeling pacing therapy, to a patient 14. While patient 14 is shown as a human, patient 14 may also be a variety of other types of animals. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22. Although the IMD 16 as depicted is configured to deliver traditional myocardial pacing therapy to one, two, or three chambers, it is to be understood that the illustrative systems, devices, and methods described herein may be utilized with other types of pacing therapy using electrodes, leads, and leadless devices to deliver pacing therapy to other portions or regions of the patients heart. For example, the illustrative systems, devices, and methods may utilize cardiac conduction system pacing where pacing is delivered to one or more portions of the patient's cardiac conduction system such as, e.g., the bundle of His, the right bundle branch, the left bundle branch, etc.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The right atrial (RA) lead 22 extends through one or more veins and the vena cava, and into the right atrium 26 of the heart 12. Further, the left ventricular (LV) coronary sinus lead 20 extends through one or more veins, the vena cava, the right atrium 26, and into the coronary sinus 30 to a region adjacent to the free wall of the left ventricle 32 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pacing rate, R-R interval, A-V delay and other various timings, pulse width, amplitude, voltage, burst length, etc. Further, the IMD 16 may be operable to use various electrode configurations to deliver pacing therapy, which may be unipolar, bipolar, quadripolar, or further multipolar. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD, or electrode apparatus. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of the heart 12 is stopped.

Figure 2:
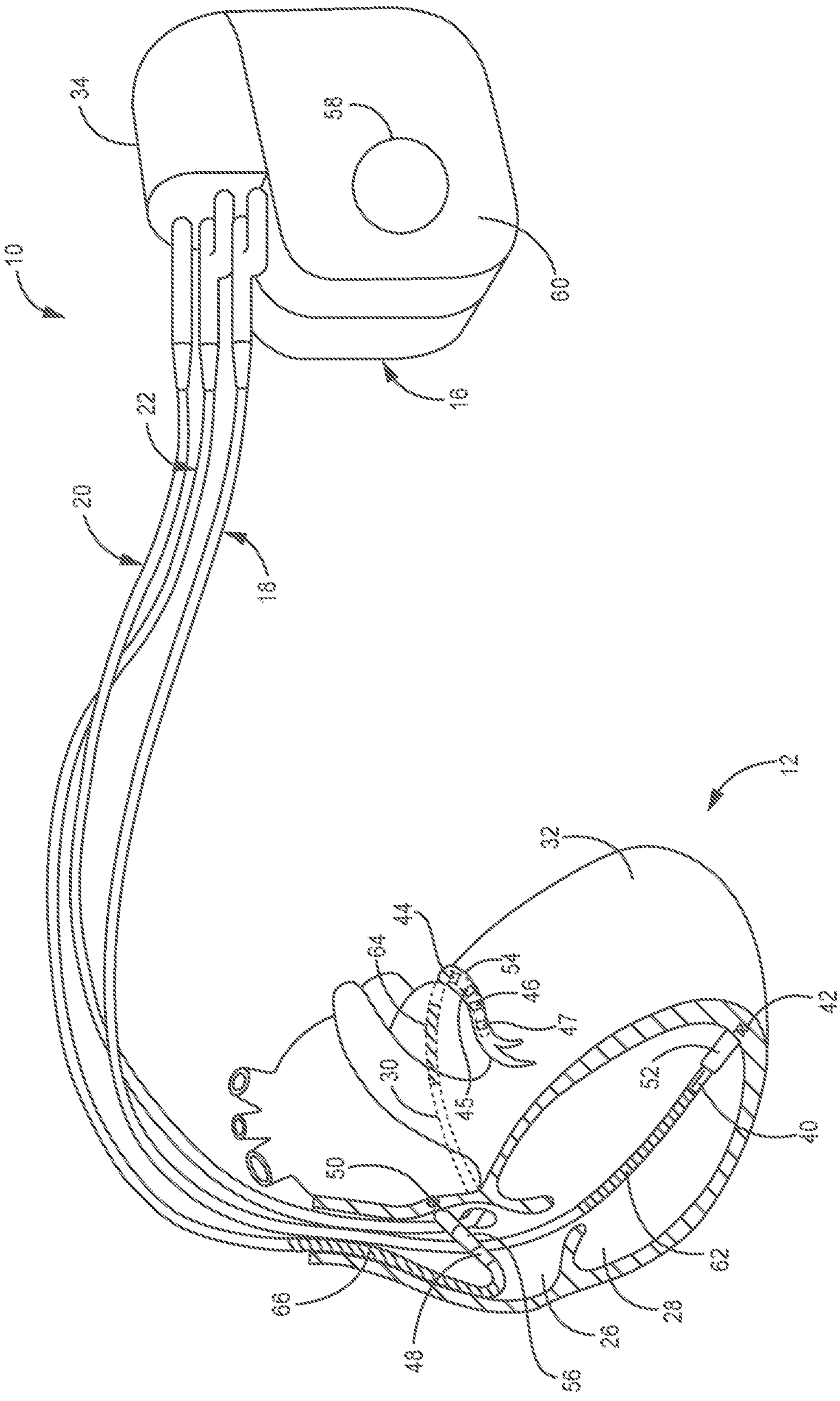
FIG. 2 is a diagram of the IMD of FIG. 1.

FIG. 2 is a conceptual diagram of the IMD 16 and the leads 18, 20, 22 of therapy system 10 of FIG. 1 in more detail. The leads 18, 20, 22 may be electrically coupled to a therapy delivery module (e.g., for delivery of support pacing therapy, cardiac remodeling pacing therapy, respiration-based pacing therapies, etc.), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 3, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The above-described configuration of the therapy system 10 is merely one example. As described herein, the illustrative systems, devices, and methods may be configured to deliver cardiac conduction system pacing therapy to one or more portions of the cardiac conduction system. Further, the illustrative systems, devices, and methods may be configured to deliver cardiac conduction system pacing therapy as well as, or in conjunction, with traditional myocardial pacing such as shown by the system 10 of FIGS. 1-2. Illustrative cardiac conduction system pacing therapy that may be utilized by the illustrative systems, devices, and methods may be described in U.S. Pat. No. 11,207,529 issued on Dec. 28, 2021, and entitled "His Bundle and Bundle Branch Pacing Adjustment," U.S. Pat. No. 7,177,704 issued on Feb. 13, 2007, and entitled "Pacing Method and Apparatus," U.S. Pat. App. Pub. No. 2022/0032062A1 published on Feb. 3, 2022, and entitled "Cardiac Conduction System Pacing," U.S. Pat. App. Pub. No. 2019/0111264A1 published on Apr. 18, 2019, and entitled "Bundle Branch Pacing Devices and Methods," each of which are incorporated herein by reference in their entireties. Moreover, in other examples, the therapy system 10 may include epicardial leads and/or patch electrodes instead of, or in addition to, the transvenous leads 18, 20, 22 illustrated in FIG. 1. In further embodiments, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 1).

Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

Other example therapy systems that provide electrical stimulation therapy to the heart 12 may include any suitable number of leads coupled to the IMD 16, and each of the leads may extend to any location within or proximate to the heart 12. Such other therapy systems may include three transvenous leads located as illustrated in FIGS. 1-2. Still further therapy systems may include a single lead that extends from the IMD 16 into the right atrium 26 or two leads that extend into a respective one of the right atrium 26 and the left atrium. In one example, the IMD 16, as a cardiac resynchronization therapy (CRT) device with a left ventricular (LV) lead may be useful for a HFpEF patient if there is a complete AV node block, as a LV lead can be more beneficial than a RV lead in such patients. In some examples, it can be desirable to deliver rate responsive pacing to the atrium for a HFpEF patient with chronotropic incompetence with an atrial lead (i.e., single chamber atrial system such as AAI) and atrial and ventricular lead system (i.e., dual chamber system such as DDD and VDD).

Figure 3A:
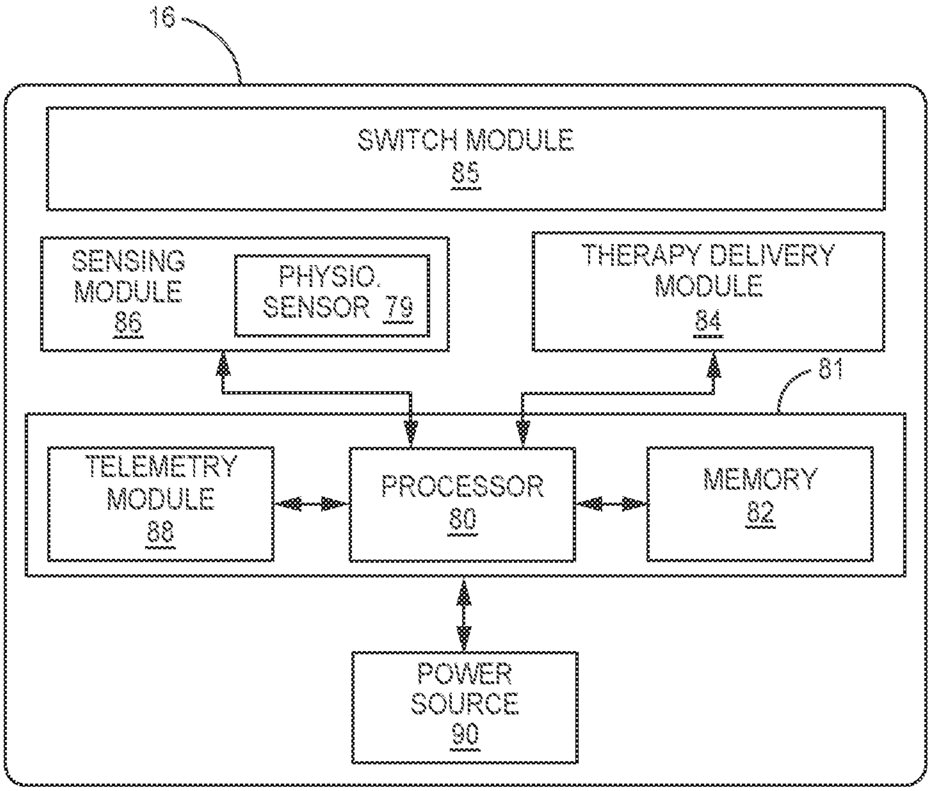
FIG. 3A is a block diagram of an IMD, e.g., of the systems of FIGS. 1-2, in accordance with embodiments described herein.

FIG. 3A is a functional block diagram of an example configuration of the IMD 16. As shown, the IMD 16 may include a control module 81, a therapy delivery module 84 (e.g., which may include a stimulation generator), a sensing module 86, and a power source 90. The control module, or apparatus, 81 may include a processor, or computing apparatus, 80, memory 82, and a telemetry module, or apparatus, 88. The memory 82 may include computer-readable instructions that, when executed, e.g., by the processor, or computing apparatus, 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically erasable programmable ROM (EEPROM), flash memory, and/or any other digital media.

The processor, or computing apparatus, 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In general, the processor, or computing apparatus, 80 may be described as including processing circuitry. In some examples, the processor, or computing apparatus, 80 may include multiple components, such as any combination of one or more microprocessors, one or more controllers, one or more DSPs, one or more ASICs, and/or one or more FPGAs, as well as other discrete or integrated logic circuitry. The functions attributed to the processor, or computing apparatus, 80 herein may be embodied as software, firmware, hardware, or any combination thereof.

The control module 81 may control the therapy delivery module, or apparatus, 84 to deliver therapy (e.g., electrical stimulation therapy such as cardiac remodeling pacing) to the heart 12 according to a selected one or more therapy programs, which may be stored in the memory 82, and based on algorithms, or methods, described further below. More specifically, the control module 81 including the processor 80 may be utilized to monitor a patient's respiration and to control a pacing rate and variables related thereto, such as a lower rate limit, to provide support pacing therapy and cardiac remodeling pacing therapy that is adjusted to restore, or provide, respiratory sinus arrhythmia as will be described further herein. Additionally, more specifically, the control module 81 including the processor 80 may control various parameters of the electrical stimulus delivered by the therapy delivery module 84 such as, e.g., A-V delays, pacing pulses with the amplitudes, pulse widths, frequency, or electrode polarities, etc., which may be specified by one or more selected therapy programs (e.g., A-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, the therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to the heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured to deliver one or more of these types of stimulation in the form of other signals, such as sine waves, square waves, and/or other substantially continuous time signals.

The IMD 16 may further include a switch module, or apparatus, 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module, or apparatus, 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switch module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

The sensing module 86, as depicted, includes a physiological sensor 79 that generates one or more signals as functions of one or more patient physiological parameters, such as activity, motion, respiration, posture, etc. In one or more embodiments, the processor 80, based on the signals generated by the sensor 79, may determine that patient 14 is within a target inactivity state so as to trigger, or initiate, cardiac remodeling pacing therapy, or conversely, determine that patient 14 is not within a target inactivity state so as to trigger or maintain support pacing therapy. Additionally, in one or more embodiments, the processor 80, based on the signals generated by the sensor 79, may determine the respiration of the patient 14. More particularly, the processor 80 may use signals and data from the sensor 79 to determine the starting points, ending points, and durations of the patient's inhalations/inspirations and exhalations/expirations.

As examples, the sensor 79 may include, or comprise, electrodes or other known sensors for detecting heart rate and respiration rate, a motion sensor, e.g., piezoelectric motion sensor, or other known sensor, that may provide evidence of a patient's activity level, etc. In some embodiments, the sensor 79 may be a multi-axis accelerometer capable of detecting motion of the patient such gross body movement and footfalls as well as the patient's posture including posture changes. Further information regarding use of multi-axis accelerometers to determine patient posture may be found in U.S. Pat. No. 5,593,431 entitled "Medical service employing multiple DC accelerometers for patient activity and posture sensing and method" and issued on Jan. 14, 1997, which is incorporated herein by reference in its entirety.

Moreover, as examples, the sensor 79 may include any suitable sensors for detecting physiologic parameters associated with respiration including oxygen level sensors (e.g., finger-tip oxygen sensors), pulse oximeter sensors, peripheral arterial tonometry sensors, carbon dioxide level sensors, impedance sensors for detecting minute ventilation (MV), pressure sensors for monitoring blood pressure or sensing airflow (breathing), microphones for monitoring breath sounds, mechanical or temperature sensors for monitoring airflow (breathing) or chest movement, thoracic effort sensors (e.g., respiratory belts worn around the chest), abdominal effort sensors (e.g., respiratory belts worn around the abdomen), any other sensor capable of monitoring a parameter indicative or predictive of the occurrence of apnea and/or hyperpnea, and any combination of these. In some embodiments, the sensor 79 may be an intracardiac sensor capable of measuring impedance between atrial and ventricular electrodes or an intrathoracic impedance sensor that measures impedance across the thorax. Additionally, the sensor 79 may also provide signals that allow the processor 80 to distinguish between inhalation/inspiration and exhalation/expiration. The sensor 79 may utilize impedance to determination respiration as described in U.S. patent application Ser. No. 17/878,557 entitled "Lead Impedance Measurement For Physiological And Device Management" and filed on Aug. 1, 2022, which is incorporated by reference herein in its entirety.

Additionally, the physiological sensor 79 may be described as including a plurality of physiological sensors, and the processor 80 may determine whether the patient 14 is within a target inactivity state based on the signals from the plurality of sensors and determine whether the patient 14 is inhaling or exhaling a breath based on the signals from the plurality of sensors. The plurality of sensors of the physiological sensor 79 may be located within a housing of IMD 16, as suggested by FIG. 3A, or coupled to IMD 16 via leads or wireless communication.

As examples, the processor 80 may determine that activity level or inactivity level of the patient 14 based on changes in signals output by the sensor 79 or based on a comparison of signals output by the sensor 79 to templates or thresholds stored in the memory 82. Illustrative activity level sensing for use in providing cardiac remodeling pacing may be described in U.S. Provisional Patent Application No. 63/304,166 entitled "Activity Detection for Cardiac Remodeling Pacing" and filed on Jan. 28, 2022, which is incorporated herein by reference in its entirety. Further, the processor 80 may determine whether patient 14 is within a target high activity state or sleeping by comparing, as examples, one or more of activity counts derived from an accelerometer or piezoelectric crystal signal, a heart rate, a heart rate variability, a respiration rate, or a respiration rate variability to threshold values stored in memory 82. Furthermore, the IMD 16 may include any of the sensors described in, and the processor 80 may determine whether patient is asleep, using any of the techniques described in U.S. Pat. No. 7,775,993 entitled "Detecting Sleep" and issued on Aug. 17, 2010, which is incorporated herein by reference in its entirety.

Further, as examples, the processor 80 may determine that respiration of the patient 14 based on changes in signals output by the sensor 79 or based on a comparison of signals output by the sensor 79 to templates or thresholds stored in the memory 82. Illustrative respiration sensing for use in providing cardiac remodeling pacing may be described in U.S. Pat. No. 7,896,813 entitled "System and Method for Monitoring Periodic Breathing Associated with Heart Failure" and issued on Mar. 1, 2011, which is incorporated herein by reference in its entirety.

In some examples, the control module 81 may operate as an interrupt-driven device and may be responsive to interrupts from pacer timing and control module, where the interrupts may correspond to the patient's respiration (e.g., inhalation and exhalation), the occurrences of sensed P-waves and R-waves, and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to a patient's respiration such as inhalation or exhalation, the processor 80 in response to a patient's activity level that may signal or indicate when to provide cardiac remodeling pacing therapy or support pacing therapy, the processor 80 in response to the occurrence of a pace or sense interrupt to determine whether the patient's heart 12 is presently exhibiting atrial or ventricular tachyarrhythmia, etc.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer or other computing device and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
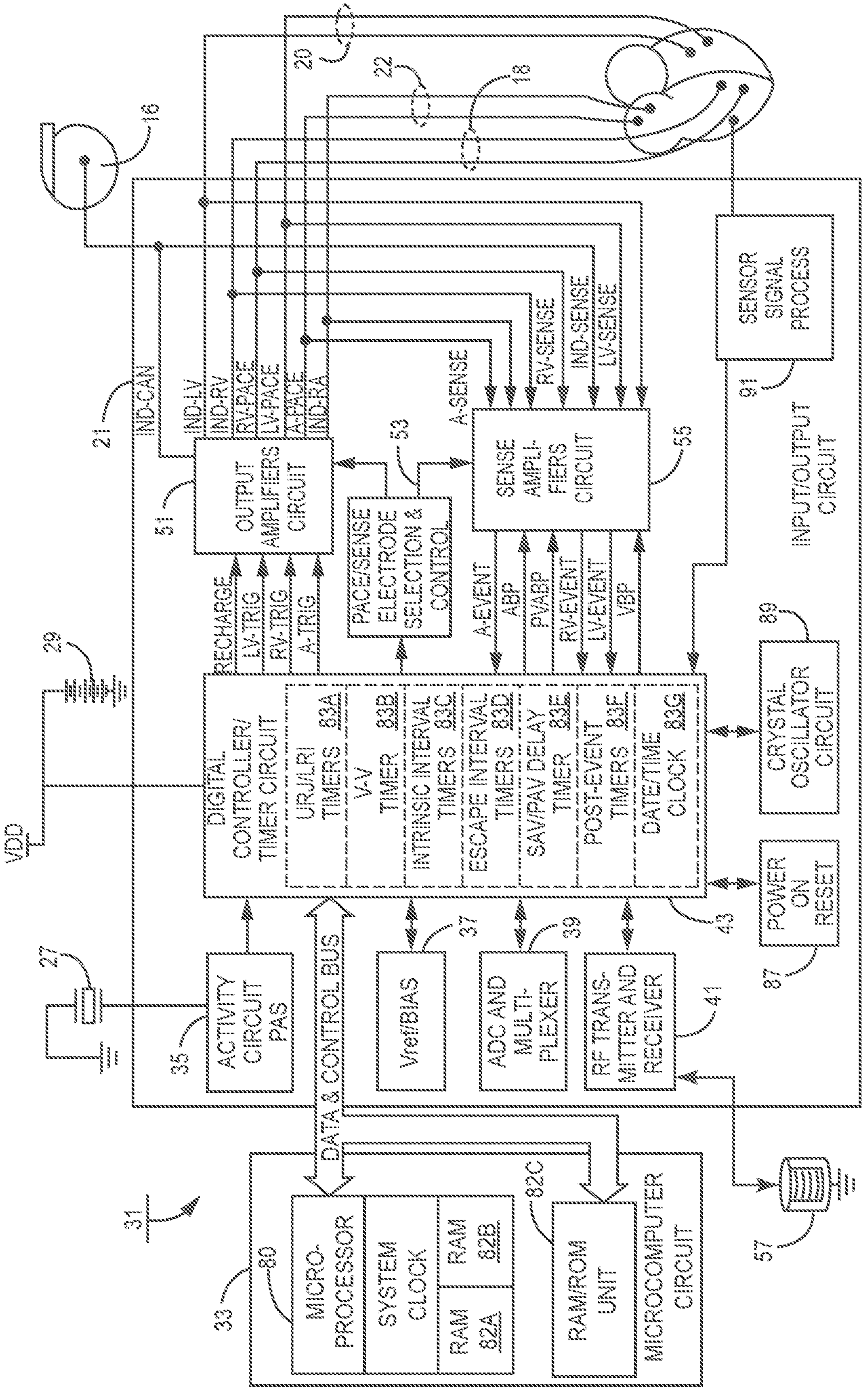
FIG. 3B is another block diagram of IMD circuitry and associated leads employed in the systems of FIGS. 1-2.

FIG. 3B is a functional block diagram for an embodiment of IMD 16 that depicts bipolar RA lead 22, bipolar RV lead 18 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the digital controller/timing circuit 43 via data and control bus to microcomputer circuitry 33. The IPG circuit 31 is illustrated in a functional block diagram divided generally into the microcomputer circuitry 33 and a pacing circuit 21. The pacing circuit 21 includes the digital controller/timing circuit 43, the output amplifiers circuit 51, the sense amplifiers circuit 55, the RF telemetry transceiver 41, the activity circuit, or patient activity sensor (PAS), 35 as well as other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Voltage reference and bias circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers circuit 55 for uplink transmission via RF telemetry transceiver 41. Voltage reference and bias circuit 37, ADC and multiplexer circuit 39, power-on-reset circuit 87, and crystal oscillator circuit 89 may correspond to any of those used in illustrative implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the activity circuit 35 in the example IPG circuit 31. The patient activity sensor 27 is coupled to the IPG housing and may take the form of a piezoelectric crystal transducer. The output signal of the patient activity sensor 27 may be processed and used as an RCP. Sensor 27 generates electrical signals in response to sensed physical activity that are processed by the activity circuit 35 and provided to digital controller/timing circuit 43. Additionally, the patient activity sensor 27 and activity circuit 35 can be used to determine whether or when to deliver cardiac remodeling pacing therapy. For example, the patient activity sensor 27 and activity circuit 35 may determine that the patient is inactive (e.g., nocturnal, resting, etc.), and thus, it may be determined to be an effective time duration for cardiac remodeling pacing therapy. Similarly, the illustrative systems, devices, and methods described herein may be practiced in conjunction with alternate types of sensors such as oxygenation sensors, pressure sensors, pH sensors, temperature sensors, respiration sensors, perfusion sensors, heart sound sensors, and heart rate sensors, for use in providing rate responsive pacing therapy, support pacing therapy, and cardiac remodeling pacing therapy capabilities. For example, impedance can be measured using a ring electrode on the lead (e.g., RA or RV lead) and temperature can be measured by a sensor at the distal end of the lead. Alternately, QT time may be used as a rate indicating parameter, in which case no extra sensor is required. Similarly, the illustrative embodiments described herein may also be practiced in non-rate responsive pacemakers.

Data transmission to and from the external programmer is accomplished by way of the telemetry antenna 57 and an associated RF telemetry transceiver 41, which serves both to demodulate received downlink telemetry and to transmit uplink telemetry. Uplink telemetry capabilities may include the ability to transmit stored digital information, e.g., activity information, rate responsive pacing profiles, operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer circuitry 33 contains a microprocessor, processor, or computing apparatus, 80 and associated system clock and on-processor RAM and ROM chips 82A and 82B, respectively. In addition, microcomputer circuitry 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in the digital controller/timing circuit 43 and A-EVENT, RV-EVENT, and LV-EVENT signals generated by sense amplifiers circuit 55, among others. The specific values of the intervals and delays timed out by the digital controller/timing circuit 43 are controlled by the microcomputer circuitry 33 by way of data and control bus from programmed-in parameter values and operating modes. In addition, if programmed to operate as a rate responsive pacemaker, a timed interrupt, e.g., every cycle or every two seconds, may be provided to allow the microprocessor to analyze the activity sensor data and update the basic pacing rate as well as A-A, V-A, as applicable. In addition, the microprocessor 80 may also serve to define variable, operative A-V delay intervals, and the energy delivered to each ventricle and/or atrium.

In one embodiment, microprocessor 80 is a custom microprocessor adapted to fetch and execute instructions stored in RAM/ROM memory 82 in a conventional manner. It is contemplated, however, that other implementations may be suitable to practice the disclosed methods. For example, an off-the-shelf, commercially available microprocessor or microcontroller, or custom application-specific, hardwired logic, or state-machine type circuit may perform the functions of microprocessor 80.

The digital controller/timing circuit 43 operates under the general control of the microcomputer circuitry 33 to control timing and other functions within the pacing circuit 21 and includes a set of timing and associated logic circuits of which certain ones pertinent to the present disclosure are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals, escape interval timers 83D for timing A-A, and/or V-A pacing escape intervals, an A-V delay interval timer 83E for timing the A-L Vp delay (or A-RVp delay) from a preceding A-EVENT or A-TRIG, a post-ventricular event timer 83F for timing post-ventricular time periods, and a date/time clock 83G.

The A-V delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery and can be based on one or more prior cardiac cycles (or from a data set empirically derived for a given patient).

The post-ventricular event timer 83F times out the post-ventricular period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer circuitry 33. The post-ventricular time periods include a post-ventricular atrial blanking period (PVARP), a post-atrial ventricular blanking period (PAVBP), a ventricular blanking period (VBP), and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates A-V delays, post-ventricular time periods, and post-atrial time periods that vary with the sensor-based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. To trigger generation of an RV-PACE or LV-PACE pulse, digital controller/timing circuit 43 may utilize the algorithms described below.

The output amplifiers circuit 51 includes switching circuits for coupling selected pace electrode pairs from among the lead conductors and the IND-CAN electrode to the RA pace pulse generator (and LA pace pulse generator if provided), RV pace pulse generator and LV pace pulse generator. Pace/sense electrode selection and control circuit 53 selects lead conductors and associated pace electrode pairs to be coupled with the atrial and ventricular output amplifiers within output amplifiers circuit 51 for accomplishing RA, LA, RV, and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. The digital controller/timing circuit 43 controls sensitivity settings of the atrial and ventricular sense amplifiers circuit 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timing circuit 43. Similarly, left atrial depolarizations or P-waves in the LA-SENSE signal that are sensed by the LA sense amplifier, if provided, result in a LA-EVENT signal that is communicated to the digital controller/timing circuit 43. Ventricular depolarizations or R-waves in the RV-SENSE signal are sensed by a ventricular sense amplifier result in an RV-EVENT signal that is communicated to the digital controller/timing circuit 43. Similarly, ventricular depolarizations or R-waves in the LV-SENSE signal are sensed by a ventricular sense amplifier result in an LV-EVENT signal that is communicated to the digital controller/timing circuit 43. The RV-EVENT, LV-EVENT, and RA-EVENT, LA-SENSE signals may be refractory or non-refractory and can inadvertently be triggered by electrical noise signals or aberrantly conducted depolarization waves rather than true R-waves or P-waves.

The techniques described in this disclosure, including those attributed to the IMD 16 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

The illustrative systems, devices, and methods of the disclosure may be described as providing respiratory-based cardiac remodeling pacing therapy in conjunction with support pacing. As used herein, cardiac remodeling pacing therapy may be described as pacing the patient's heart at an increased rate above what the patient's heart is presently beating at to provide, or cause, cardiac remodeling of physical structures of the patient's heart such as, e.g., increasing compliance of the left ventricle walls, thinning of the left ventricle walls, dilation of the left ventricle walls, etc. As used herein, support pacing therapy may be described as cardiac pacing where the patient's heart rate is monitored and the patient's heart rate is prevented from falling below a defined a lower rate limit. In other words, the support pacing does not allow a patient's heart rate to be below the lower rate limit by delivering pacing to keep the patient's heart rate above or at the lower rate limit.

The respiratory-based cardiac remodeling pacing therapy in conjunction with support pacing may be used to treat HF patients, and in particular, HFpEF patients. As described herein, the cardiac remodeling pacing may provide an increase in heart rate that can lead to left ventricle wall thinning, dilatation, and increase in compliance thereof. Myocyte cell loss and myocyte reactive hypertrophy may be major components of ventricular remodeling in pacing-induced dilated cardiomyopathy. Such cardiac remodeling may be desirable for patients with HFpEF since such patients have a normal-sized ventricle with an increased wall thickness. In some embodiments, cardiac remodeling pacing may be defined as overdrive pacing as cardiac remodeling pacing increases the heart rate (i.e., tachycardia pacing) to cause the cardiac remodeling (e.g., increased compliance of left ventricle walls, thinning of left ventricle walls, etc.). Details regarding cardiac remodeling pacing may be further provided in U.S. Patent Application Publication No. 2019/0381323A1 entitled "Delivery of Cardiac Pacing Therapy for Cardiac Remodeling" and published on Dec. 19, 2019, which is herein incorporated by reference in its entirety.

It may be optimal to deliver cardiac remodeling pacing during selected opportunities such as when the patient is at rest (e.g., while the patient is at rest or resting during the day, at night, etc.). Moreover, the cardiac remodeling pacing may be described as opportunistic high-rate pacing during the day while maintaining high-rate pacing at night. For example, the cardiac remodeling pacing may utilize a higher rate (e.g., higher than 100 beats per minute, or at least 110 beats per minute) of pacing for longer periods (e.g., more than five hours or at least six hours) of time during times of low activity (e.g., at night) and additionally other opportunistic pacing can be provided during the day, for a total more than ten hours (e.g., about 12 hours) of pacing therapy.

Figure 4:
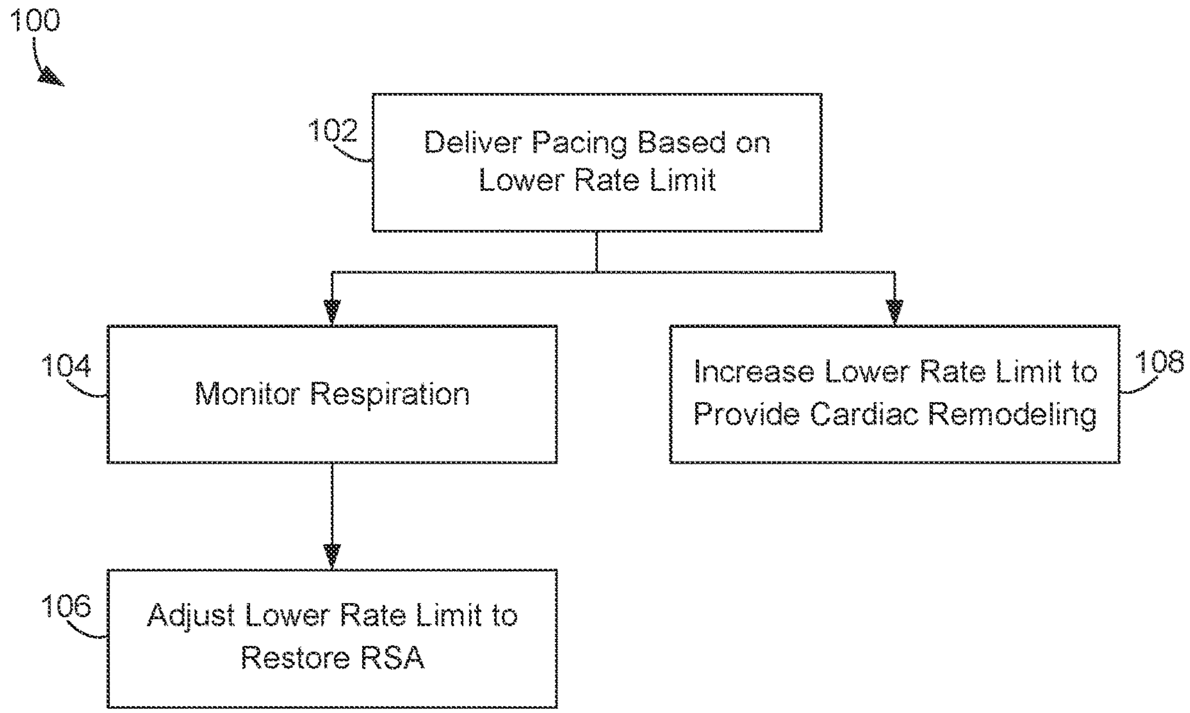
FIG. 4 is a flow diagram that illustrates one example of a method of performing respiratory-based cardiac remodeling pacing therapy.

An illustrative method 100 of performing respiratory-based cardiac remodeling pacing therapy is depicted in FIG. 4. The method 100 can be performed by the processor, microprocessor, or computing apparatus 80, the physiological sensor 79, and any other element or portion of the IMD 16 described herein with reference to FIGS. 1-3. It is to be understood that the illustrative method 100 and processes described therein may be performed on non-implantable devices or subdermal implanted devices, which may communicate with pacing devices to deliver the support pacing and cardiac remodeling pacing. For example, the illustrative method 100 may be performed by an external device (e.g., outside of the patient's body) but may communicate with an IMD to deliver the pacing. Additionally, although the method 100 is depicted using blocks and arrows extending from some blocks to other blocks, it is to be understood that the blocks and functionality, methods steps, and processes associated therewith do not necessarily need to be performed sequentially, and thus, one or more of the blocks and functionality, methods steps, and processes associated therewith may be performed simultaneously and repeatedly.

The method 100 may include delivering pacing 102 based on a lower rate limit. The lower rate limit may be described as being the minimum pacing rate being delivered at a particular time or during a particular pacing mode. The lower rate limit may be adjusted or modified depending on the pacing therapy mode that the pacing device is configured in. The initial lower rate limit may be set to a minimum lower rate limit that is between about 60 beats per minute (bpm) and about 100 bpm. It is to be understood that the minimum lower rate limit may be patient specific. For example, a patient's physician may determine the minimum lower rate limit based on the condition of the patient. The pacing 102 may be delivered, e.g., using the systems and devices described herein with reference to FIGS. 1-3.

The method 100 may further include monitoring a patient's respiration 104. For example, the patient's respiration may be monitored 104 using a respiration sensor such as, for example, the physiological sensor 79 described herein with reference to FIG. 3A. The delivery of pacing 102 and the monitoring of a patient's respiration 104 may occur at the same time and independent from one another. In other words, the delivery of pacing 102 may not be dependent on the monitoring of a patient's respiration 104, and conversely, the monitoring of a patient's respiration 104 may not be dependent on the delivery of pacing 102.

Monitoring a patient's respiration 104 may include determination a patient's inhalations/inspirations and exhalations/expirations. More specifically, one or more of a starting point (e.g., beginning, initiation, start time, etc.) of a patient's inhalation/inspiration, an end point (e.g., end, cessation, end time, etc.) of a patient's inhalation/inspiration, a starting point (e.g., beginning, initiation, start time, etc.) of a patient's exhalation/expiration, an end point (e.g., end, cessation, end time, etc.) of a patient's exhalation/expiration, an inhalation/inspiration duration (e.g., time period, time duration, etc.) of a patient's inhalation/inspiration, and an exhalation/expiration duration (e.g., time period, time duration, etc.) of a patient's exhalation/expiration may be determined based on the monitoring of the patient's respiration 104.

The patient's respiration may be used adjust the lower rate limit based on the patient's respiration to restore, or achieve, respiratory sinus arrhythmia (RSA) 106. For example, the lower rate limit may be increased during exhalation, and the lower rate limit may be decreased during inhalation to, e.g., result in mimicking or initiating respiratory sinus arrhythmia. The adjustment of the lower rate limit may be made, or initiated, at the starting point (e.g., outset or beginning) of the inhalation or exhalation. For example, the starting point of the inhalation or exhalation may trigger, or initiate, the lower rate limit adjustment or modification.

In at least one embodiment, the lower rate limit may be increased or decreased by a selected value such as a RSA value or amplitude. The RSA value, or amplitude, may be between about 5 bpm and about 30 bpm. In one embodiment, the RSA value is 15 bpm. In some embodiments, the RSA value may be one or more of greater than or equal to 5 bpm, greater than or equal to 7 bpm, greater than or equal to 10 bpm, greater than or equal to 13 bpm, less than or equal to 30 bpm, less than or equal to 25 bpm, less than or equal to 22 bpm, less than or equal to 20 bpm, less than or equal to 17 bpm, etc.

For example, if the present lower rate limit is 80 bpm and the RSA value is 15 bpm, the lower rate limit may be increased by 15 bpm during exhalation (e.g., during the time period within which exhalation is occurring) to 95 bpm. Thus, during exhalation, the present lower rate limit is 95 bpm. Following the exhalation, during the next inhalation (e.g., during the time period within which inhalation is occurring), the lower rate limit of 95 bpm may be decreased by the RSA value of 15 bpm such that the lower rate limit is 80 bpm.

In some embodiments, the RSA value or amplitude may be described in terms of a percentage of the lower rate limit. For example, the RSA value may be between about 5% and about 30% of the lower rate limit. In this way, the lower rate limit may be increased and decreased by a percentage of itself. In one embodiment, the RSA value is 20%. In some embodiments, the RSA value may be one or more of greater than or equal to 5%, greater than or equal to 10%, greater than or equal to 15%, less than or equal to 30%, less than or equal to 25%, less than or equal to 20%, etc.

In some embodiments, the RSA value may be based on one or more measurable physiological parameters of the patient. For example, the RSA value may be based on one or more of the patient's heart rate, respiration rate, and activity level. More specifically, the illustrative systems, devices, and methods may monitor, or measure, one or more of the patient's heart rate, respiration rate, and activity level, and then generate, or compute, the RSA value based on the one or more of the patient's heart rate, respiration rate, and activity level. In other words, the RSA may be a function of one or more measurable physiological parameters of the patient such as, e.g., the patient's heart rate, respiration rate, and activity level. For example, the RSA value may decrease as one or more heart rate, respiration rate, and activity level increase.

Additionally, in one or more embodiments, a different RSA value may be determined and used for each of the support pacing therapy and the cardiac remodeling pacing therapy. For instance, the RSA value used for the cardiac remodeling pacing therapy may be less than the RSA value used for the support pacing therapy. Thus, the illustrative systems, devices, and methods may utilize a support RSA value to be used for adjust the lower rate limit during support pacing to restore respiratory sinus arrhythmia and may utilize a remodeling RSA value to be used for adjust the lower rate limit during cardiac remodeling pacing to restore respiratory sinus arrhythmia wherein the remodeling RSA value is less than the support RSA value. For example, the support RSA value may be 15 bpm and the remodeling RSA value may be 7 bpm. Further, for example, the support RSA value may be 20% of the lower rate limit for support pacing, and the remodeling RSA value may be 5% of the lower rate limit for cardiac remodeling pacing.

Additionally, the method 100 may also include increasing the lower rate limit to provide cardiac remodeling pacing 108. For example, the lower rate limit may be increased to a cardiac remodeling pacing rate (which may be a maximum lower rate limit less a RSA value or amplitude). The cardiac remodeling pacing rate may be a pacing rate that provides optimal cardiac remodeling pacing therapy during time periods when it is determined that cardiac remodeling pacing should be delivered to the patient. Such time periods when it is determined that cardiac remodeling pacing should be delivered to the patient may be referred to as remodeling time periods. The remodeling time periods may be initiated, or triggered, during night time when the patient is asleep and during day time when the patient is inactive or at rest. The initiation of remodeling time periods may be determined based on various types of activity sensing. Illustrative activity level sensing for use in providing cardiac remodeling pacing may be described in U.S. Provisional Patent Application No. 63/304,166 entitled "Activity Detection for Cardiac Remodeling Pacing" and filed on Jan. 28, 2022, which is incorporated herein by reference in its entirety. The remodeling time periods may be between about 5 minutes and about 8 hours. Additionally, the remodeling time periods may be patient specific and set, or configured, by a physician.

The cardiac remodeling pacing rate may be between about 80 bpm and about 140 bpm. It is to be understood that the cardiac remodeling pacing rate may be patient specific. For example, a patient's physician may determine the cardiac remodeling pacing rate based on the condition of the patient. The cardiac remodeling pacing rate may be about 50% to about 85% of a patient's maximum heart rate. Regardless, the cardiac remodeling pacing rate will always be greater than the initial or minimum lower rate limit at which support pacing therapy is being delivered. After the expiration of the remodeling time period, the lower rate limit may be decreased back to the initial or minimum lower rate limit to provide support pacing therapy.

Although the lower rate limit has been increased or set to the cardiac remodeling pacing rate during the delivery of cardiac remodeling pacing 108, the lower rate limit may still be adjusted to restore respiratory sinus arrhythmia 106. More specifically, the lower rate limit, which is set to the cardiac remodeling pacing rate during the cardiac remodeling pacing therapy, may be increased during exhalation and decreased during inhalation. The increase during exhalation and the decrease during inhalation may be by the RSA value or amplitude as previously described herein.

Figure 5:
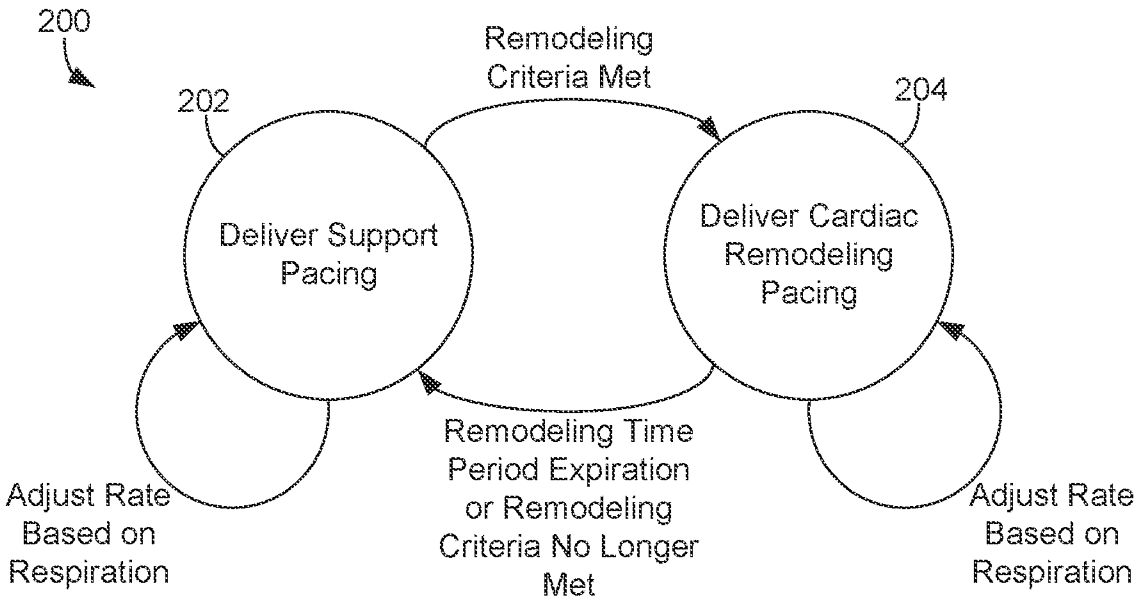
FIG. 5 is a state diagram that illustrates another example of a method of performing respiratory-based cardiac remodeling pacing therapy.

Thus, it is to be understood that the method 100 provides support pacing and cardiac remodeling pacing while also providing adjustment of the lower rate limit to restore respiratory sinus arrhythmia during both pacing therapies. Another example of a method of performing respiratory-based cardiac remodeling pacing therapy 200 is depicted in FIG. 5. The method 200 is similar to the method of claim 100 but depicted and described with respect to a state diagram.

The method 200 includes two states: namely, delivery of support pacing 202 and delivery of cardiac remodeling pacing 204, each of which being substantially similar to the support pacing and cardiac remodeling pacing described herein with respect to FIG. 4. The method 200 may initiate or begin in delivery of support pacing 202. In other words, the default state of the method 200 may be the delivery of support pacing 202. The support pacing 202 may be delivered using a lower rate limit as described previously, which may be set, or configured, to a minimum lower rate limit or support pacing rate (e.g., 75 bpm).

When remodeling criteria is met, the method 200 may switch from the delivery of support pacing 202 to the delivery of cardiac remodeling pacing 204. The remodeling criteria may include one or more factors or elements such as, e.g., activity level, time of day, etc. For example, if it is during the day and the patient's activity is low indicating that the patient is resting, the method 200 may switch from the delivery of support pacing 202 to the delivery of cardiac remodeling pacing 204. Further, for example, if it is during the night and the patient's activity is low indicating that the patient is asleep, the method 200 may switch from the delivery of support pacing 202 to the delivery of cardiac remodeling pacing 204.

As described herein, the cardiac remodeling pacing 204 may include an increased lower rate limit such as to a cardiac remodeling pacing rate (e.g., 130 bpm) to provide the cardiac remodeling. If the remodeling time period expires or the remodeling criteria is no longer met, the method 200 may switch from the delivery of cardiac remodeling pacing 204 to the delivery of support pacing 202, wherein the lower rate limit may again be adjusted to the minimum lower rate limit or support pacing rate.

As shown, both of the support pacing 202 and the cardiac remodeling pacing 204 may be adjusted based on respiration. More specifically, both of the lower rate limit/support pacing rate utilized during the support pacing 202 and the lower rate limit/cardiac remodeling pacing rate of the cardiac remodeling pacing 204 may be adjusted according to the inhalation and exhalation of the patient based on a RSA value or amplitude.

When the methods 100, 200 are transitioning from support pacing therapy to cardiac remodeling pacing therapy, or vice versa, the lower rate limit may be adjusted gradually from the present value to the new value. For example, when transitioning from support pacing therapy to cardiac remodeling pacing therapy, the lower rate limit may be increased gradually according to an increasing ramp rate until the lower rate limit is equal to a cardiac remodeling pacing rate. Further, for example, when transitioning from cardiac remodeling pacing therapy to support pacing therapy, the lower rate limit may be decreased gradually according to a decreasing ramp rate until the lower rate limit is equal to the minimum lower rate limit or support pacing rate. The magnitudes, or absolute values, of the increasing ramp rate and the decrease ramp rate may be the same or different. Further, the magnitude, or absolute value, of the increasing ramp rate may be greater than the magnitude, or absolute value, of the decreasing ramp rate. The ramp rate may be expressed in terms of beats per minute (bpm) per number of cardiac cycle. In other words, the lower rate limit may be increased or decreased by the bpm of the ramp rate after the number of cardiac cycles. The ramp rate may be between about 1 bpm per 8 cardiac cycles and about 5 bpm per 1 cardiac cycle. In one embodiment, the increasing ramp rate is 1 bpm per 4 cardiac cycles. In one embodiment, the decreasing ramp rate is 1 bpm per 1 cardiac cycle. In other embodiments, the ramp rate may be one or more of greater than or equal to 1 bpm per 8 cardiac cycles, greater than or equal to 1 bpm per 6 cardiac cycles, greater than or equal to 1 bpm per 6 cardiac cycles, greater than or equal to 1 bpm per 4 cardiac cycles, greater than or equal to 1 bpm per 2 cardiac cycles, greater than or equal to 1 bpm per 1 cardiac cycle, less than or equal to 5 bpm per 1 cardiac cycle, less than or equal to 4 bpm per 1 cardiac cycle, and less than or equal to 2 bpm per 1 cardiac cycle.

Figure 6:
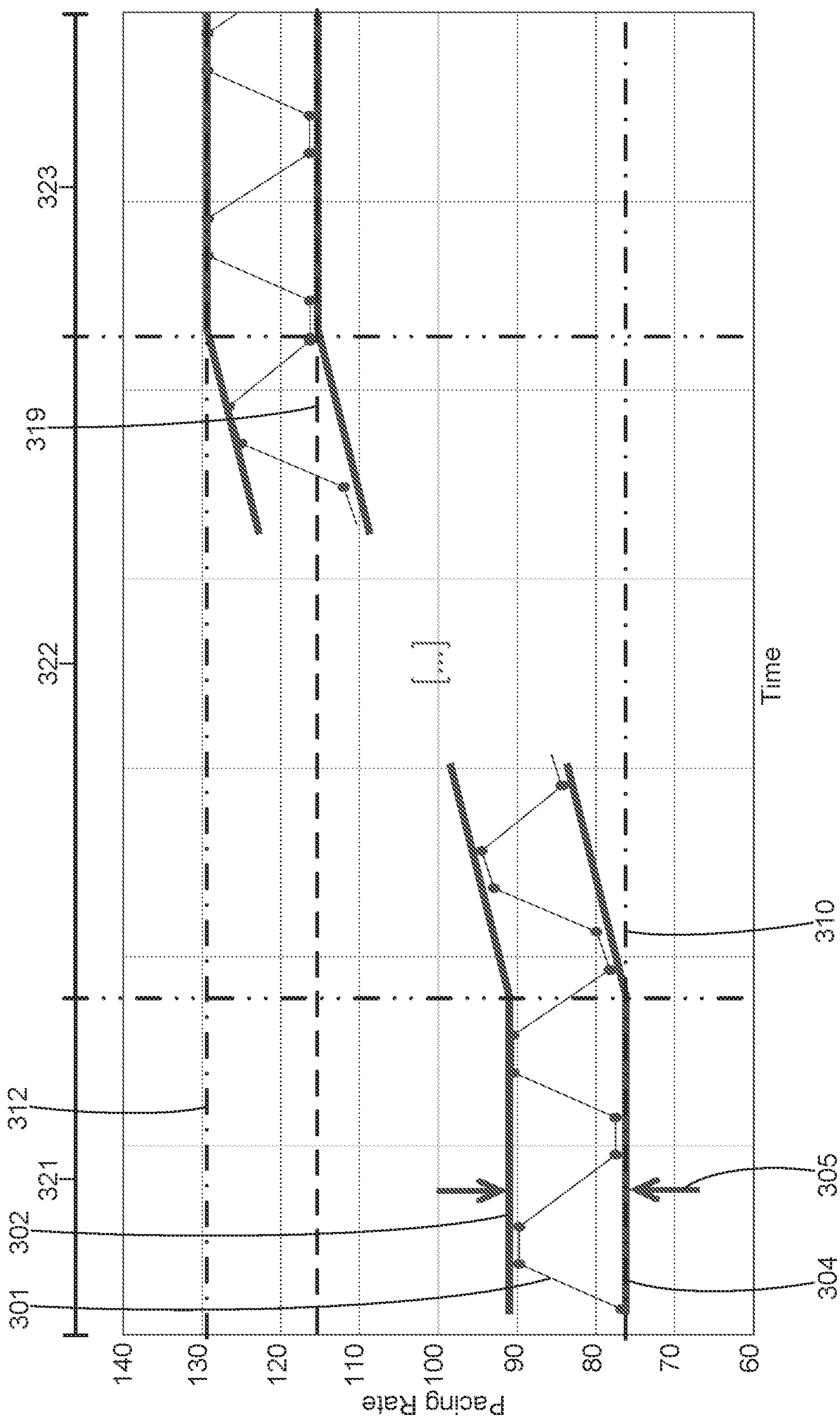
FIG. 6 is a graph of pacing rate over time illustrating an example of respiratory-based cardiac remodeling pacing therapy.

A graph of pacing rate over time illustrating an example of respiratory-based cardiac remodeling pacing therapy is depicted in FIG. 6. The minimum lower rate limit is indicated by a lower dot-dash horizontal line 310, the maximum lower rate limit is indicated by a dot-dash horizontal line 312, and the cardiac remodeling pacing rate is indicated by a dashed horizontal line 319. In this example, the minimum lower rate limit is 77 bpm, the maximum lower rate limit is 129 bpm, and the cardiac remodeling pacing rate is 116 (e.g., the maximum lower rate limit minus the RSA value or amplitude). The present pacing rate being used by the support pacing and cardiac remodeling pacing is indicated by a solid thin line 301. The solid black lines 302, 304 bounding the present pacing rate 301 represent the upper and lower limits of the present pacing rate when adjusted by a RSA value or amplitude 305. In this example, the RSA value 305 is 13 bpm.

As shown, support pacing is being delivered during a support pacing time period 321, the present pacing rate is transitioning from support pacing to cardiac remodeling pacing during a ramp time period 322 (e.g., ramp rate defines the slope), and cardiac remodeling pacing is being delivered during a cardiac remodeling pacing time period 323. In each of the time periods 321, 322, 323, the present pacing rate 301 is shown to be adjusted by the RSA value, or amplitude, 305 during exhalation and inhalation. For example, the present pacing rate 301 is shown as being increased and decreased during each of the time periods 321, 322, 323 according to the patient's respiration. In other words, no matter which pacing mode (even including ramping from one mode to another mode), the present pacing rate 301 is shown to be adjusted by the RSA value, or amplitude, to achieve or restore respiratory sinus arrhythmia. Additionally, it is to be understood that the same concepts apply when "ramping "down" from cardiac remodeling pacing to support pacing.

By implementing the illustrative systems, devices, and methods in accordance with various embodiments, cardiac remodeling pacing, or overdrive, pacing can be provided for longer periods of time, leading to fewer missed opportunities for pacing and improved patient outcomes.

While the present disclosure is not so limited, an appreciation of various aspects of the disclosure will be gained through a discussion of the specific examples and illustrative embodiments provided below. Various modifications of the examples and illustrative embodiments, as well as additional embodiments of the disclosure, will become apparent herein.

EXAMPLES

Example Ex1: An implantable medical device comprising:

- a pacing electrode to be positioned proximate the patient's heart to deliver pacing therapy to the patient's heart;
- a respiration sensor to determine the patient's respiration rate; and
- a computing apparatus operably coupled to the pacing electrode and the respiration sensor, the computing apparatus configured to:
- deliver pacing using at least the pacing electrode based on a lower rate limit,
  - monitor the patient's respiration the respiration sensor,
  - adjust the lower rate limit based on the patient's respiration to restore respiratory sinus arrhythmia (RSA), and
  - increase the lower rate limit to provide cardiac remodeling pacing during remodeling time periods.

Example Ex2: A method comprising:

- delivering pacing to a patient's heart based on a lower rate limit;
- monitoring the patient's respiration;
- adjusting the lower rate limit based on the patient's respiration to restore respiratory sinus arrhythmia (RSA); and
- increasing the lower rate limit to provide cardiac remodeling pacing during remodeling time periods.

Example Ex 3: The device as in Example Ex1 or the method of Example Ex2, wherein adjusting the lower rate limit based on the patient's respiration rate to restore RSA comprises:

- determining exhalation based on the patient's monitored respiration;
- increasing the lower rate limit during exhalation by a RSA value;

determining inhalation based on the patient's monitored respiration; and decreasing the lower rate limit during inhalation by the RSA value.

Example Ex4: The device or method as in Example Ex3, wherein the RSA value is less than or equal to 15 beats per minute.

Example Ex5: The device or method as in Examples Ex3-Ex4, wherein the RSA value is based on one or more of the patient's heart rate, respiration rate, and activity level.

Example Ex6: The device or method as in Examples Ex3-Ex5, wherein the computing apparatus is further configured execute or the method further comprises decreasing the RSA value for cardiac remodeling pacing.

Example Ex7: The device or method as in Examples Ex1-Ex6, wherein increasing the lower rate limit to provide cardiac remodeling pacing during remodeling time periods comprises increasing the lower rate limit to a cardiac remodeling pacing rate.

Example Ex8: The device or method as in Example Ex7, wherein the cardiac remodeling pacing rate is greater than or equal to 100 beats per minute.

Example Ex9: The device or method as in Examples Ex1-Ex8, wherein increasing the lower rate limit to provide cardiac remodeling pacing during remodeling time periods comprises gradually increasing the lower rate limit according to ramp rate until the lower rate limit is equal to a cardiac remodeling pacing rate.

Example Ex10: The device or method as in Example Ex9, wherein the ramp rate is greater than or equal to 1 beat per minute increase for every 8 cardiac cycles.

Example Ex11: The device or method as in Examples Ex1-Ex10, wherein the lower rate limit is initially set to a minimum lower rate limit, wherein the minimum lower rate limit is greater than or equal to 60 beats per minute.

Example Ex12: The device or method as in Examples Ex1-Ex11, wherein delivering pacing based on the lower rate limit comprises delivering cardiac conduction system pacing therapy based on the lower rate limit.

Example Ex13: The device or method as in Examples Ex1-Ex12, wherein the computing apparatus is further configured to execute or the method further comprises initiating the cardiac remodeling pacing in response to inactive times periods when the patient is inactive or asleep.

Example Ex14: An implantable medical device comprising:

a pacing electrode to be positioned proximate a patient's heart to deliver pacing therapy to the patient's heart;

a respiration sensor to determine a respiration rate of the patient; and a computing apparatus operably coupled to the pacing electrode and the respiration sensor, the computing apparatus configured to:

switch between delivering support pacing using at least the pacing electrode based on a support pacing rate or delivering cardiac remodeling pacing using at least the pacing electrode to provide cardiac remodeling based on a cardiac remodeling pacing rate, wherein the cardiac remodeling pacing rate is greater than the support pacing rate;

monitor the patient's respiration rate using the respiration sensor; and adjust the cardiac remodeling pacing rate and the support pacing rate based on the patient's respiration rate to restore respiratory sinus arrhythmia (RSA).

Example Ex15: A method comprising:

switching between delivering support pacing based on a support pacing rate or delivering cardiac remodeling pacing to provide cardiac remodeling based on a cardiac remodeling pacing rate, wherein the cardiac remodeling pacing rate is greater than the support pacing rate;

monitoring the patient's respiration rate; and adjusting the cardiac remodeling pacing rate and the support pacing rate based on the patient's respiration rate to restore respiratory sinus arrhythmia (RSA).

Example Ex16: The device of Example Ex14 or the method of Example Ex15, wherein adjusting the cardiac remodeling pacing rate and the support pacing rate on the patient's respiration rate to restore RSA comprises:

determining exhalation based on the patient's monitored respiration;

increasing the cardiac remodeling pacing rate and the support pacing rate during exhalation by a RSA value;

determining inhalation based on the patient's monitored respiration; and decreasing the cardiac remodeling pacing rate and the support pacing rate during inhalation by the RSA value.

Example Ex17: The device or method as in Example Ex6, wherein the RSA value is less than or equal to 15 beats per minute.

Example Ex18: The device or method as in Examples Ex16-Ex17, wherein the RSA value is based on one or more of the patient's heart rate, respiration rate, and activity level.

Example Ex19: The device or method as in Examples Ex16-Ex18, wherein the computing apparatus is further configured execute or the method further comprises decreasing the RSA value for cardiac remodeling pacing.

Example Ex20: The device or method as in Examples Ex14-Ex19, the cardiac remodeling pacing rate is greater than or equal to 100 beats per minute.

Example Ex21: The device or method as in Examples Ex14-Ex20, wherein switching between delivering support pacing using at least the pacing electrode based on a support pacing rate or delivering cardiac remodeling pacing using at least the pacing electrode to provide cardiac remodeling based on a cardiac remodeling pacing rate comprises:

when switching from the support pacing to the cardiac remodeling pacing, gradually increasing the support pacing rate until it equals the cardiac remodeling pacing rate according to an increasing ramp rate; and when switching from the cardiac remodeling pacing to the support pacing, gradually decreasing the cardiac remodeling pacing rate until it equals the support pacing rate over a decreasing ramp rate.

Example Ex22: The device or method as in Example Ex21, wherein a magnitude of the increasing ramp rate is greater than a magnitude of the decreasing ramp rate.

Example Ex23: The device or method as in Examples Ex14-Ex22, wherein the support pacing rate is greater than or equal to 75 beats per minute.

Example Ex24: The device or method as in Examples Ex14-Ex23, wherein delivering pacing based on the lower rate limit comprises delivering cardiac conduction system pacing therapy based on the lower rate limit.

Example Ex25: The device or method as in Examples Ex14-Ex24, wherein the computing apparatus is further configured to execute or the method further comprises initiating the cardiac remodeling pacing in response to inactive times periods when the patient is inactive or asleep.

What is claimed:

1. An implantable medical device comprising:

a pacing electrode to be positioned proximate a patient's heart to deliver pacing therapy to the patient's heart;

a respiration sensor to determine the patient's respiration rate; and a computing apparatus operably coupled to the pacing electrode and the respiration sensor, the computing apparatus configured to:

deliver pacing to the patient's heart using at least the pacing electrode based on a lower rate limit, wherein the lower rate limit is a minimum pacing rate delivered to the patient, monitor the patient's respiration using the respiration sensor, adjust the lower rate limit based on the patient's respiration to restore respiratory sinus arrhythmia (RSA), and initiate cardiac remodeling pacing comprising increasing the lower rate limit, wherein the cardiac remodeling pacing is configured to provide or cause cardiac remodeling of physical structures of the patient's heart.

2. The device of claim 1, wherein adjusting the lower rate limit based on the patient's respiration rate to restore RSA comprises:

determining exhalation based on the patient's monitored respiration;

increasing the lower rate limit during exhalation by a RSA value;

determining inhalation based on the patient's monitored respiration; and decreasing the lower rate limit during inhalation by the RSA value.

3. The device of claim 2, wherein the RSA value is less than or equal to 15 beats per minute.

4. The device of claim 2, wherein the RSA value is based on one or more of the patient's heart rate, respiration rate, and activity level.

5. The device of claim 2, wherein the computing apparatus is further configured to decrease the RSA value during the cardiac remodeling pacing.

6. The device of claim 1, wherein increasing the lower rate limit comprises increasing the lower rate limit to a cardiac remodeling pacing rate.

7. The device of claim 6, wherein the cardiac remodeling pacing rate is greater than or equal to 100 beats per minute.

8. The device of claim 1, wherein increasing the lower rate limit comprises gradually increasing the lower rate limit according to ramp rate until the lower rate limit is equal to a cardiac remodeling pacing rate.

9. The device of claim 8, wherein the ramp rate is greater than or equal to 1 beat per minute increase for every 8 cardiac cycles.

10. The device of claim 1, wherein the lower rate limit is initially set to a minimum lower rate limit, wherein the minimum lower rate limit is greater than or equal to 60 beats per minute.

11. The device of claim 1, wherein the pacing electrode to be positioned proximate a portion of the cardiac conduction system of the patient's heart to deliver cardiac conduction system pacing therapy to the patient's heart, wherein delivering pacing using at least the pacing electrode based on the lower rate limit comprises delivering cardiac conduction system pacing therapy using at least the pacing electrode based on the lower rate limit.

12. The device of claim 1, wherein the cardiac remodeling pacing is initiated in response to inactive times periods when the patient is inactive or asleep.

13. A method comprising:

delivering pacing to a patient's heart based on a lower rate limit, wherein the lower rate limit is a minimum pacing rate delivered to the patient;

monitoring the patient's respiration;

adjusting the lower rate limit based on the patient's respiration to restore respiratory sinus arrhythmia (RSA); and initiating cardiac remodeling pacing comprising increasing the lower rate limit, wherein the cardiac remodeling pacing is configured to provide or cause cardiac remodeling of physical structures of the patient's heart.

14. The method of claim 13, wherein adjusting the lower rate limit based on the patient's respiration rate to restore RSA comprises:

determining exhalation based on the patient's monitored respiration;

increasing the lower rate limit during exhalation by a RSA value;

determining inhalation based on the patient's monitored respiration; and decreasing the lower rate limit during inhalation by the RSA value.

15. The method of claim 14, wherein the RSA value is less than or equal to 15 beats per minute.

16. The method of claim 14, wherein the RSA value is based on one or more of the patient's heart rate, respiration rate, and activity level.

17. The method of claim 14, wherein the method further comprises decreasing the RSA value during the cardiac remodeling pacing.

18. The method of claim 13, wherein increasing the lower rate limit comprises increasing the lower rate limit to a cardiac remodeling pacing rate.

19. The method of claim 18, wherein the cardiac remodeling pacing rate is greater than or equal to 100 beats per minute.

20. The method of claim 13, wherein increasing the lower rate limit comprises gradually increasing the lower rate limit according to ramp rate until the lower rate limit is equal to a cardiac remodeling pacing rate.

21. The method of claim 20, wherein the ramp rate is greater than or equal to 1 beat per minute increase for every 8 cardiac cycles.

22. The method of claim 13, wherein the lower rate limit is initially set to a minimum lower rate limit, wherein the minimum lower rate limit is greater than or equal to 60 beats per minute.

23. The method of claim 13, wherein delivering pacing to a patient's heart based on the lower rate limit comprises delivering cardiac conduction system pacing therapy to the patient's cardiac conduction system based on the lower rate limit.

24. The method of claim 13, wherein the cardiac remodeling pacing is initiated in response to inactive times periods when the patient is inactive or asleep.

25. An implantable medical device comprising:

a pacing electrode to be positioned proximate a patient's heart to deliver pacing therapy to the patient's heart;

a respiration sensor to determine a respiration rate of the patient; and a computing apparatus operably coupled to the pacing electrode and the respiration sensor, the computing apparatus configured to:

switch between delivering support pacing to the patient's heart using at least the pacing electrode based on a support pacing rate or delivering cardiac remodeling pacing to the patient's heart using at least the pacing electrode to provide cardiac remodeling based on a cardiac remodeling pacing rate, wherein the cardiac remodeling pacing rate is greater than the support pacing rate, wherein the cardiac remodeling pacing is configured to provide or cause cardiac remodeling of physical structures of the patient's heart;

monitor the patient's respiration rate using the respiration sensor; and adjust the cardiac remodeling pacing rate and the support pacing rate based on the patient's respiration rate to restore respiratory sinus arrhythmia (RSA).

26. The device of claim 25, wherein adjusting the cardiac remodeling pacing rate and the support pacing rate on the patient's respiration rate to restore RSA comprises:

determining exhalation based on the patient's monitored respiration;

increasing the cardiac remodeling pacing rate and the support pacing rate during exhalation by a RSA value;

determining inhalation based on the patient's monitored respiration; and decreasing the cardiac remodeling pacing rate and the support pacing rate during inhalation by the RSA value.

27. The device of claim 26, wherein the RSA value for cardiac remodeling pacing is less than the RSA value for support pacing.

28. The device of claim 25, wherein switching between delivering support pacing using at least the pacing electrode based on a support pacing rate or delivering cardiac remodeling pacing using at least the pacing electrode to provide cardiac remodeling based on a cardiac remodeling pacing rate comprises:

when switching from the support pacing to the cardiac remodeling pacing, gradually increasing the support pacing rate until it equals the cardiac remodeling pacing rate according to an increasing ramp rate; and when switching from the cardiac remodeling pacing to the support pacing, gradually decreasing the cardiac remodeling pacing rate until it equals the support pacing rate according to a decreasing ramp rate.

29. The device of claim 28, wherein a magnitude of the increasing ramp rate is greater than a magnitude of the decreasing ramp rate.

30. The device of claim 25, wherein computing apparatus is further configured to determine patient activity, wherein switching between delivering support pacing using at least the pacing electrode based on a support pacing rate or delivering cardiac remodeling pacing using at least the pacing electrode to provide cardiac remodeling based on a cardiac remodeling pacing rate comprises:

switching from the support pacing to the cardiac remodeling pacing in response to determination of patient inactivity or that the patient is asleep.

* * * * *